United States Patent
Zhou et al.

(10) Patent No.: US 9,629,598 B2
(45) Date of Patent: Apr. 25, 2017

(54) SYSTEM AND METHOD FOR AUTO-CONTOURING IN ADAPTIVE RADIOTHERAPY

(71) Applicant: IMPAC Medical Systems, Inc., Sunnyvale, CA (US)

(72) Inventors: Yan Zhou, Saint Peters, MO (US); Xiao Han, Chesterfield, MO (US); Nicolette Patricia Magro, Cornelius, NC (US)

(73) Assignee: IMPAC Medical Systems, Inc., Sunnycale, CA (US)

( * ) Notice: Subject to any disclaimer, the term of this patent is extended or adjusted under 35 U.S.C. 154(b) by 92 days.

(21) Appl. No.: 14/192,778

(22) Filed: Feb. 27, 2014

(65) Prior Publication Data

US 2015/0238158 A1    Aug. 27, 2015

(51) Int. Cl.
*G06T 7/00* (2006.01)
*A61B 6/00* (2006.01)

(52) U.S. Cl.
CPC .......... *A61B 6/5205* (2013.01); *A61B 6/5217* (2013.01); *G06T 7/0012* (2013.01); *G06T 7/0042* (2013.01); *G06T 7/0083* (2013.01); *G06T 7/0089* (2013.01)

(58) Field of Classification Search
None
See application file for complete search history.

(56) References Cited

U.S. PATENT DOCUMENTS

| | | | | |
|---|---|---|---|---|
| 2008/0069436 | A1* | 3/2008 | Orderud | G06T 7/20 382/154 |
| 2008/0101676 | A1* | 5/2008 | Zheng | A61B 6/503 382/131 |
| 2008/0267468 | A1* | 10/2008 | Geiger | A61B 8/13 382/128 |
| 2009/0080728 | A1* | 3/2009 | Socher | G06K 9/6256 382/128 |
| 2009/0136108 | A1* | 5/2009 | Badiei | G06T 7/0083 382/131 |
| 2010/0259546 | A1* | 10/2010 | Yomdin | G06T 7/0083 345/473 |

(Continued)

OTHER PUBLICATIONS

Zhan, Yiqiang, Maneesh Dewan, and Xiang Sean Zhou. "Cross modality deformable segmentation using hierarchical clustering and learning." In Medical Image Computing and Computer-Assisted Intervention—MICCAI 2009, pp. 1033-1041. Springer Berlin Heidelberg, 2009.*

(Continued)

*Primary Examiner* — Sumati Lefkowitz
*Assistant Examiner* — Carol Wang
(74) *Attorney, Agent, or Firm* — Finnegan, Henderson, Farabow, Garrett & Dunner, LLP

(57) ABSTRACT

A method for performing automatic contouring in a medical image. The method may include receiving an image containing a region of interest and determining a first contour of the region of interest using a boundary detector. The method may include refining the first contour based on a shape dictionary to generate a second contour of the region of interest and updating at least one of the boundary detector or the shape dictionary based on the second contour.

20 Claims, 6 Drawing Sheets

(56) References Cited

U.S. PATENT DOCUMENTS

| | | | |
|---|---|---|---|
| 2011/0054295 A1* | 3/2011 | Masumoto | A61B 5/055 600/407 |
| 2011/0058720 A1* | 3/2011 | Lu | G06T 7/0032 382/131 |
| 2011/0222750 A1* | 9/2011 | Liao | A61B 6/487 382/131 |
| 2011/0263979 A1* | 10/2011 | El-Aklouk | A61B 8/14 600/438 |
| 2013/0034276 A1* | 2/2013 | Hibbard | G06T 17/30 382/128 |
| 2013/0129174 A1* | 5/2013 | Grbic | G06T 7/0012 382/131 |

OTHER PUBLICATIONS

Zhang, Shaoting, Yiqiang Zhan, and Dimitris N. Metaxas. "Deformable segmentation via sparse representation and dictionary learning." Medical Image Analysis 16, No. 7 (2012): 1385-1396.*

Zheng, Yefeng, Adrian Barbu, Bogdan Georgescu, Michael Scheuering, and Dorin Comaniciu. "Four-chamber heart modeling and automatic segmentation for 3-D cardiac CT volumes using marginal space learning and steerable features." Medical Imaging, IEEE Transactions on 27, No. 11 (2008): 1668-1681.*

Zhou, Yan, Shaoting Zhang, Nikolaos Tsekos, Ioannis Pavlidis, and Dimitris Metaxas. "Left endocardium tracking via collaborative trackers and shape prior." In Biomedical Imaging (ISBI), 2012 9th IEEE International Symposium on, pp. 784-787. IEEE, 2012.*

Zhang, Shaoting, Yiqiang Zhan, Yan Zhou, Mustafa Uzunbas, and Dimitris N. Metaxas. "Shape prior modeling using sparse representation and online dictionary learning." In Medical Image Computing and Computer-Assisted Intervention—MICCAI 2012, pp. 435-442. Springer Berlin Heidelberg, 2012.*

Zhou, Yan. "Tracking the left ventricle through collaborative trackers and sparse shape model." In MICCAI Workshop on Sparsity Techniques in Medical Imaging. 2012.*

International Search Report and Written Opinion in corresponding PCT Application No. PCT/IB2015/051383 dated Sep. 29, 2015 (12 pages).

Hill, A et al., "Model-Based Image Interpretation Using Genetic Algorithms." Image and Vision Computing 10(5):295-300 (1992).

Dollár, P et al., "Structured Forests for Fast Edge Detection." 2013 IEEE International Conference on Computer Vision, 1841-1848 (2013).

Zhou, D et al., "Automatic Landmark Location with a Combined Active Shape." Biometrics: Theory, Applications, and Systems, (2009) (7 pages).

Roth, P et al., "Incremental Robust Learning an Active Shape Model." (2006) retrieved from URL:http://lrs.icg.tugraz.at/pubs/roth_aapr_06.pdf on Sep. 4, 2015 (8 pages).

Mukherjee, T. "Active Shape Models for Medical Images Segmentation." (2012) retrieved from URL:http://ganymed.imib.rwth-aachen.de/lehmann/seminare/SMBV12_06.pdf on Sep. 4, 2015 (7 pages).

Cootes, T.F. et al., "Active Shape Models—Their Training and Application." Computer Vision and Image Understanding 61(1):38-59 (1995).

* cited by examiner

SYSTEM AND METHOD FOR AUTO-CONTOURING IN ADAPTIVE RADIOTHERAPY

TECHNICAL FIELD

The present disclosure relates generally to medical imaging and treatment. More specifically, the present disclosure relates to systems and methods for auto-contouring medical images in radiotherapy procedures.

BACKGROUND

In radiotherapy procedures, a patient usually needs to take a series of 3D CT images for planning and treatment at different stages of disease. To generate a new plan, a physician often needs to contour an image from scratch, which can be time consuming and also lacks consistency with previous contours/plans. Moreover, during treatment, the shapes and locations of contoured organs are usually different from those in the planning image due to changing organ condition during treatment. Directly adopting the plan does not always produce precise dose delivery for optimal treatment. Therefore, it is crucial to have an automatic contouring method to adaptively adjust the contours of the new scans on the fly. It would not only reduce contouring time for the physicians, but also improve the accuracy and consistency for treatment delivery.

Among all the organs under cancer treatment, prostate is a very important one in male pelvic region but very difficult for auto-contouring. Main challenges include: (1) low contrast in 3D CT images, which makes a large portion of the prostate boundary nearly invisible (see FIG. 1); (2) image artifacts produced by prostate seeds (see FIGS. 1(a) and (c)); (3) large area of gas/feces/coil filled in the rectum (see FIG. 1(b), (d), and (e)); and (4) unpredictable prostate condition in different treatment stages.

Currently when making a new plan or during treatment, physicians usually do not utilize the same patient's previous plans or incorporate a patient's previous plans to make a new plan/treatment. Even when previous plans are used, previous plans are incorporated by registration to map the previous contours to the current image. One common method is rigid registration, this method, however, only provides a few degrees of freedom. Thus, the registered contour may not be precise. Deformable registration may be employed to improve the accuracy by calculating non-linear organ deformations. In general, the accuracy of the contour may depend on the number of reference images (atlases) used. There is, however, an increased computational cost in proportion to the number of reference images (atlases) used, which makes it difficult to use for online adaptive planning.

Therefore, it is desirable to develop a new method and system to perform auto-contouring in medical images accurately and efficiently.

SUMMARY

One embodiment of the disclosure is directed to a method, implemented by a processor, for performing auto-contouring in a medical image. The method may include receiving an image containing a region of interest and determining, by the processor, a first contour of the region of interest using a boundary detector. The method may also include refining, by the processor, the first contour based on a shape dictionary to generate a second contour of the region of interest. The method may include updating at least one of the boundary detector or the shape dictionary based on the second contour.

In various embodiments, the method may include one or more of the following features: refining, by the processor, the second contour may include using the boundary detector; determining, by the processor, the first contour may include determining whether an image point of the image is on a boundary of the region of interest; and selecting a set of image points that are determined to be on the boundary of the region of interest to form the first contour; determining whether the image point of the image is on the boundary of the region of interest may include determining a probability of the image point being on the boundary, and selecting the set of image points to form the first contour includes selecting image points having probabilities higher than a predetermined threshold; refining, by the processor, the first contour based on the shape dictionary to generate the second contour may include selecting a set of shapes from the shape dictionary; combining the selected set of shapes to approximate the first contour; and generating the second contour based on the combined set of shapes; the method may include determining whether at least a subset of image points on the first contour are on the second contour by minimizing an optimization function; updating at least one of the boundary detector or the shape dictionary based on the second contour may include updating the boundary detector and (a) after updating the boundary detector based on the second contour, determining an updated first contour, (b) refining the updated first contour based on the shape dictionary to generate an updated second contour, and repeating steps (a) and (b) until at least one of the following conditions is met: a number of repetitions reaches a predetermined value, or a residual error reaches a predetermine minimum; updating at least one of the boundary detector or the shape dictionary based on the second contour may include updating the boundary detector, wherein updating the boundary detector may include comparing the image having the second contour with a collection of images containing the region of interest, selecting a subset of images from the collection similar to the image having the second contour, and updating the boundary detector based on the image having the second contour and the selected subset of images; updating the boundary detector based on the image having the second contour and the selected subset of images may include: segregating positive and negative image points, selecting positive image points located on the second contour or on boundaries of the selected subset of images, extracting steerable features from the selected positive image points, determining a feature vector based on the extracted steerable features, and updating the boundary detector based on the feature vector; and updating at least one of the boundary detector or the shape dictionary based on the second contour may include updating the shape dictionary, wherein updating the shape dictionary includes: selecting a subset of shapes from the image containing the second contour, obtaining a sparse coefficient for each shape in the subset, and updating the shape dictionary based on the obtained sparse coefficients.

Another embodiment of the disclosure is directed to a system for performing auto-contouring in a medical image. The system may include a processor, and memory operatively coupled to the processor and storing instructions that when executed by the processor, causes the processor to perform a method. The method may include receiving an image containing a region of interest; determining a first contour of the region of interest using a boundary detector; refining the first contour based on a shape dictionary to generate a second contour of the region of interest; and updating at least one of the boundary detector or the shape dictionary based on the second contour.

In various embodiments, the system may include one or more of the following features: the method performed by the processor may include determining whether an image point of the image is on a boundary of the region of interest, and selecting a set of image points that are determined to be on the boundary of the region of interest to form the first contour; the method may include determining a probability of the image point being on the boundary, and selecting image points having probabilities higher than a predetermined threshold; the method may include selecting a set of shapes from the shape dictionary; combining the selected set of shapes to approximate the first contour; and generating the second contour based on the combined set of shapes; the method may include determining whether at least a subset of image points on the first contour are on the second contour by minimizing an optimization function; updating at least one of the boundary detector or the shape dictionary based on the second contour may include updating the boundary detector, and (a) after updating the boundary detector based on the second contour, determining an updated first contour; (b) refining the updated first contour based on the shape dictionary to generate an updated second contour; and repeating steps (a) and (b) until at least one of the following conditions is met: a number of repetitions reaches a predetermined value; or a residual error reaches a predetermine minimum; the method may include refining the second contour using the boundary detector.

Another embodiment of the disclosure is directed to a computer-implemented method for training a boundary detector based on a plurality of medical images containing a region of interest. The method may include selecting, by a processor, image points located on boundaries of the region of interest from the plurality of medical images; extracting, by the processor, steerable features from the selected image points; determining, by the processor, a feature vector based on the extracted steerable features; and generating, by the processor, the boundary detector based on the feature vector.

In various embodiments, the method may include one or more of the following features: comparing a new image having a new contour with the plurality of medical images; selecting a subset of medical images from the plurality based on their similarities to the new image having the new contour; and updating the boundary detector based on the new image having the new contour and the selected subset of medical images; selecting a subset of shapes from the new image containing the new contour; obtaining a sparse coefficient for each shape in the subset; and updating a shape dictionary based on the obtained sparse coefficient.

The preceding summary and the following detailed description are exemplary only and do not limit the scope of the claims.

BRIEF DESCRIPTION OF THE DRAWINGS

The accompanying drawings, which are incorporated in and constitute a part of this specification, in connection with the description, illustrate various embodiments and exemplary aspects of the disclosed embodiments. In the drawings.

DESCRIPTION OF EXEMPLARY EMBODIMENTS

Reference will now be made in detail to exemplary embodiments, examples of which are illustrated in the accompanying drawings. When appropriate, the same reference numbers are used throughout the drawings to refer to the same or like parts.

In this disclosure, a learning-based system and corresponding method for auto-contouring in adaptive radiotherapy are introduced. In particular, a population-based boundary detector and a population-based sparse shape dictionary can be trained. The trained boundary detector and the sparse shape dictionary can then be used to perform auto-contouring in a patient's planning image. As more treatment images are collected, the system may automatically update the boundary detector and the sparse shape dictionary to incorporate patient-specific information. Once a new treatment image is received, the system may perform auto-contouring of the interested organ on the fly.

Figure 1:
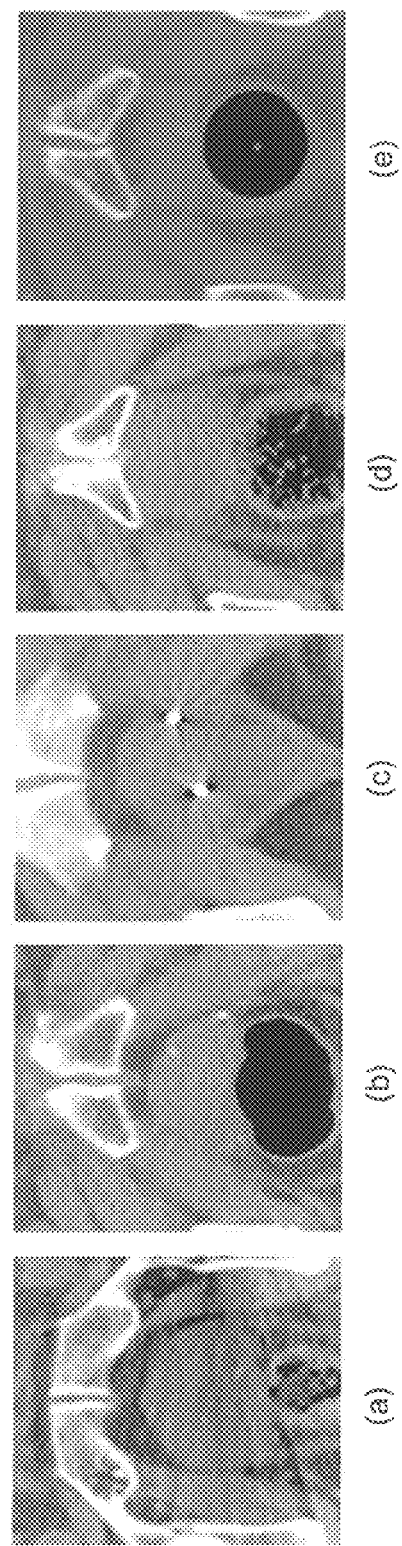
FIG. 1 shows exemplary medical images of the prostate.

One advantage of this approach is its high accuracy. In the online auto-contouring stage, the method may achieve an average DICE of 0.93 on the prostate. Another advantage of this approach is it can handle bad quality images (e.g., images shown in FIG. 1) quite well, because consistent artifacts/low quality can be learned and treated as part of the patient-specific knowledge. Additionally, this method is computationally efficient when applying to a new image, because the model updating process can be performed off-line and fully automatically, which can be done any time when the machine is vacant. Online auto-contouring can take the same amount of time regardless of how many images are collected for training. This is advantageous over a deformable registration method which requires multiple atlases, where the amount of auto-contouring time increases in proportion to the number of atlases used. As a result, the disclosed learning-based system can produce accurate auto-contouring results. The off-line training and updating processes can be fully automatic. The on-line auto-contouring process can be computationally efficient. The system can handle images of any quality, which is well suited for the adaptive radiotherapy in clinics.

Figure 2:
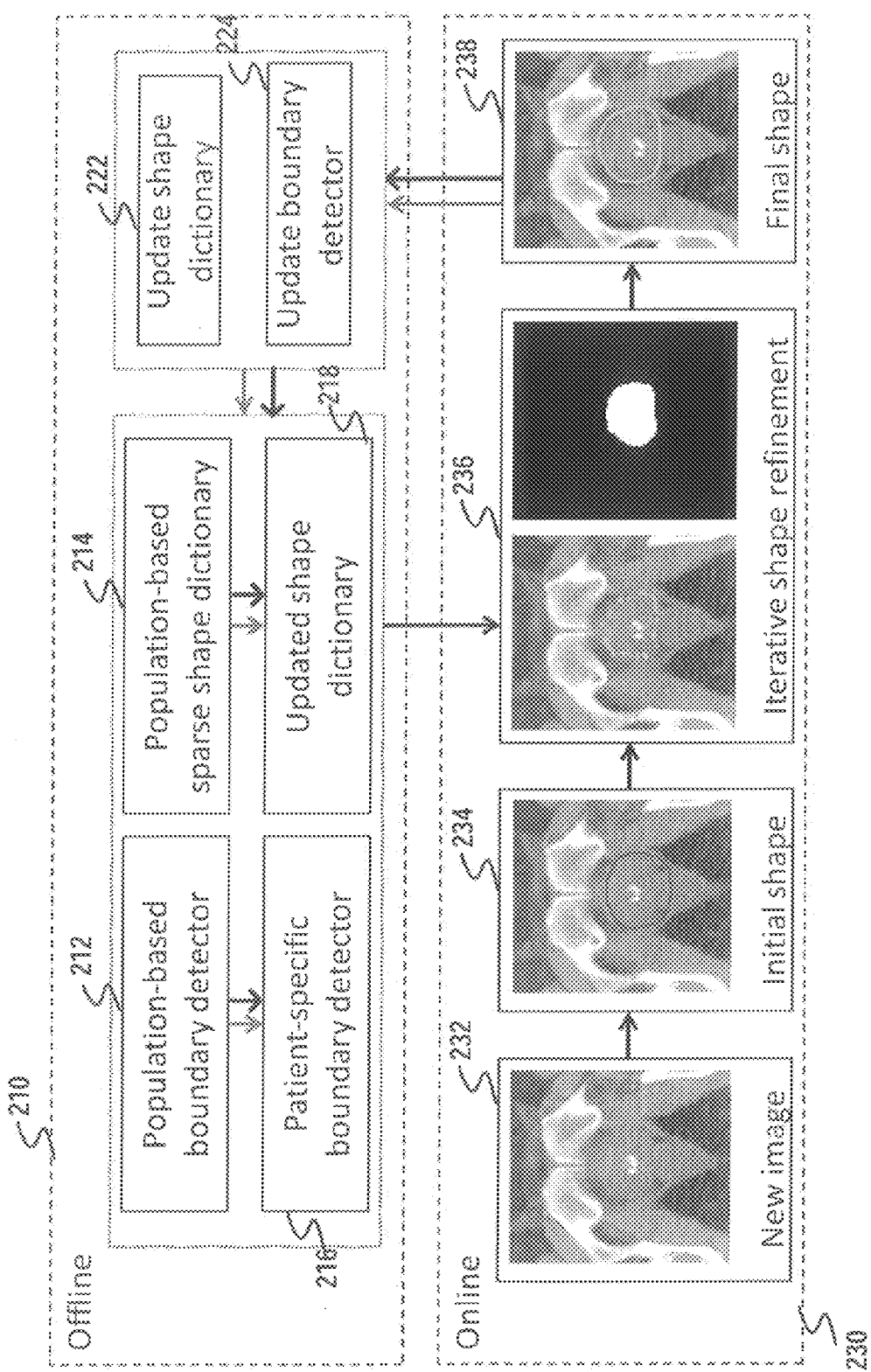
FIG. 2 shows an exemplary workflow of an auto-contouring system, according to an embodiment of the present invention.

FIG. 2 shows an exemplary workflow of the auto-contouring system. The top part shows the steps for off-line training/updating, while the bottom part shows the online auto-contouring components. Algorithm flow involved in off-line training/updating is marked with double-arrows. Algorithm flow involved in online auto-contouring process is marked with single-arrows.

Population-Based Boundary Detector

In order to detect the boundary surface of a prostate in a new image, the offline part of the system (210) first trains a population-based boundary detector 212. From a set of patients' images, the system may collect positive and negative samples according to, for example, the manual contours provided by experts. Boundary voxels on the contours may be selected as positive samples, while voxels far away from the contour may be selected as negative samples. For each training sample, 3D steerable features can be extracted and stored as a feature vector. Random Forest algorithm may be used to train the boundary detector on the collected samples. Once the boundary detector is generated, for each upcoming image, the system may search along the normal direction of an initialized shape, and may use the boundary detector to decide for each point if it is on the boundary or not. The boundary detector may return a probability of that point being on the boundary. Among all the points in the search range, the points with the highest probability, or with the probability higher than a predetermined threshold, may be selected as the new boundary points.

Population-Based Sparse Shape Refinement

The detected 3D boundaries from the boundary detector may be quite noisy. To reduce the noise, a sparse shape model may be used to refine the detected boundaries. In some embodiments, a population-based sparse shape dictionary 214 may be employed as the shape prior to inferring the detected boundary shape. Sparse shape dictionary 214 may select a sparse set of 3D shapes in the shape dictionary and compose them together to approximate the first contour and refine an input shape (e.g., the detected boundaries). This method leverages two sparsity observations of the input shape instance: (1) the input shape can be approximately represented by a sparse linear combination of shapes in the shape dictionary; and (2) parts of the input shape may contain gross errors but such errors are sparse. This method may alleviate three problems of shape prior modeling, i.e., modeling complex shape variations, handling non-Gaussian errors, and preserving local detail information of the input shape.

For each refinement iteration, the method may adopt an algorithm to minimize the following optimization function:

$$\underset{x,e,\beta}{\operatorname{argmin}} \|T(v_S, \beta) - SDx - Se\|_2^2 + \gamma_1\|x\|_1 + \gamma_2\|e\|_1 \quad (1)$$

Where $v_S$ is a subset of points on the input shape, D is the shape dictionary that represents all training shapes, $T(v_S, \beta)$ is a global transformation operator with parameter $\beta$, which aligns the input shape to the same space of D. In the equation, x denotes the weight coefficient of the linear combination, and e is a vector that modes the large residual errors. S is a binary diagonal matrix which indicates if the a certain point is in the subset $v_S$. Here, S is the detected boundary locations represented by their x,y,z coordinates in the 3D CT images. The solved shape is then sent back to the boundary detector 212 for another round of shape refinement. The iterative process stops once (1) it reaches a certain number of iterations (e.g., 10 iterations); or (2) it reaches a certain minimal residual error.

Adapting Patient-Specific Information

Once a new treatment image (e.g., new image 232) is collected, it may be necessary to update the boundary detector 212 and the sparse shape dictionary 214 to incorporate patient-specific information and generate a patient-specific boundary detector 216 and an updated shape dictionary 218, respectively. For the patient-specific boundary detector 216, the system may compare the current image with a set of collected patients' images, and picked a set of patient images that are similar to the current image. The same patient's previous images can be selected as most similar images, but images from other patients who have similar image structure may also be selected. The selected patient images may be used for updating the boundary detector to form the patient-specific boundary detector 216. The updating process is off-line (e.g., updating processes 222 and 224) and doesn't require human intervention.

While updating the boundary detector can be quite efficient, because not so many images are required for training the boundary detector, updating the sparse shape dictionary to generate an updated shape dictionary 218 may be quite computationally costly. To handle large shape variations even from the same patient, a general shape dictionary that can comprehensively capture shape variations in the shape space is necessary, thus it may be undesirable to limit the number of training shapes. However, it may also be desirable to include the patient's recent images to the shape dictionary to cover patient-specific information. To avoid training the shape dictionary from scratch, which is very time consuming, and to improve the computational efficiency, dictionary learning techniques can be employed. For example, an online learning method can be used to adaptively and efficiently incorporate new shapes. When new training shapes come, instead of re-constructing the shape dictionary from scratch, the system may update the shape dictionary using a block-coordinates descent approach. Using the dynamically updated dictionary, the sparse shape model can be gracefully scaled up to model shapes from a large number of training shapes without sacrificing run-time efficiency. In one embodiment, this method starts from constructing an initial shape dictionary using the K-SVD algorithm. When new shape comes, it iteratively employs two stages until converge: sparse coding and dictionary updating. Sparse coding aims to find the sparse coefficient for each signal, the dictionary update stage aims to update the dictionary based on all discovered coefficients. Based on stochastic approximation, the dictionary can be updated efficiently using block-coordinates descent method. This is a parameter-free method and does not require any learning rate tuning. It is important to note that in the dictionary updating step, instead of requiring all training shapes, the system may only exploit a small batch of newly acquired data. In this way, the shape dictionary can be efficiently updated online using new data as selected. Using this online updated dictionary, the run-time efficiency of shape composition is not sacrificed with more training shapes. In addition, the method can be gracefully scaled-up to contain shape priors from, theoretically, infinite number of training shapes.

Online Auto-Contouring

Online auto-contouring may start with an initial shape (e.g., initial shape 234 in FIG. 2). In one embodiment, DEMONS method with single atlas can be used to get the initial contour. For each voxel on the surface of the initial contour, the system (e.g., the online part of the system 230) may search along its normal direction and apply the boundary detector 212 to find the voxel with highest boundary probability or with probability higher than a predetermined threshold. Then the system may use the sparse shape dictionary 214 to refine the 3D detected boundary surface (e.g., refinement 236 in FIG. 2). Classification and refinement can be applied for several iterations to get more accurate results (e.g., final shape 238).

Figure 3:
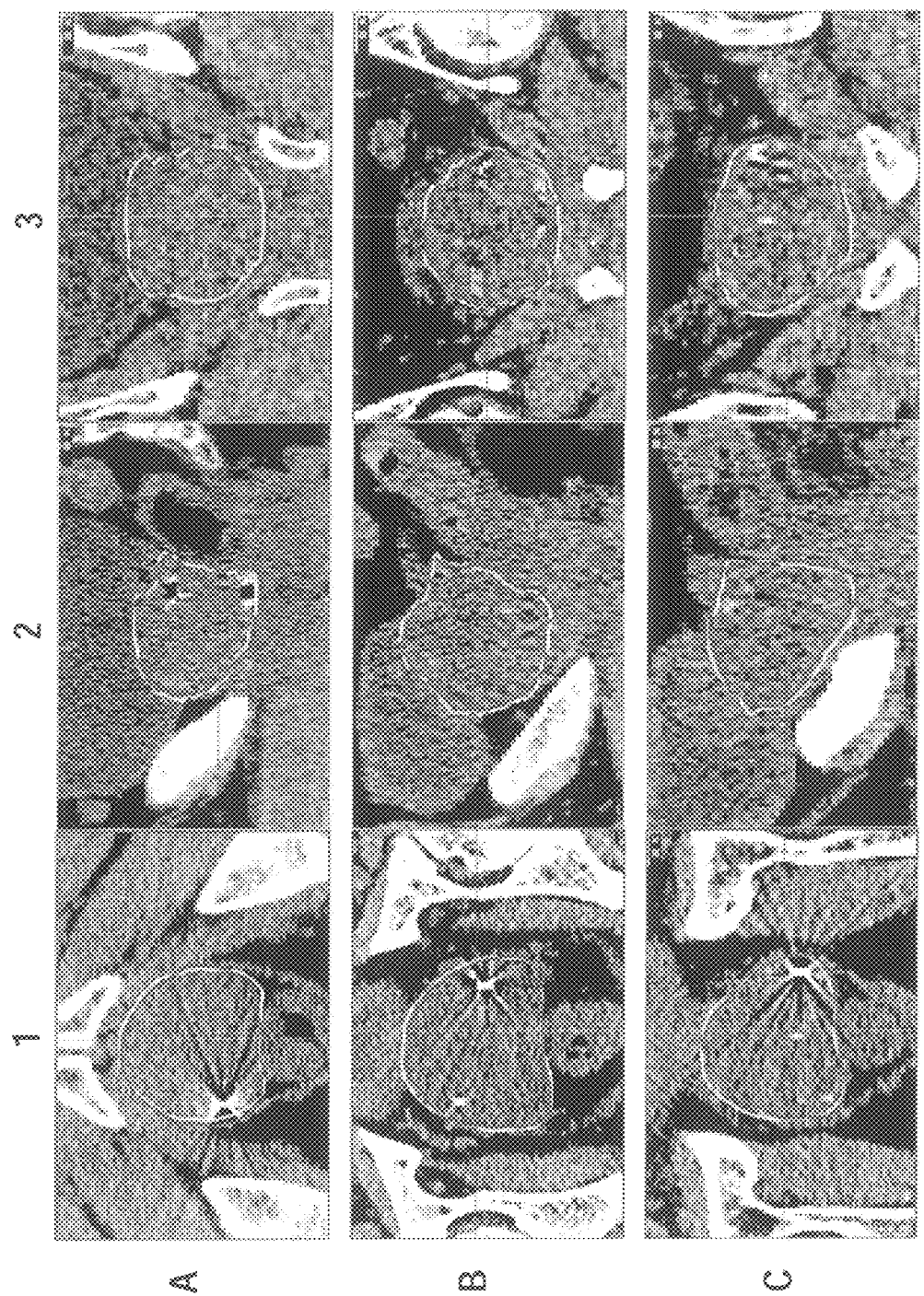
FIG. 3 shows exemplary auto-contouring results, according to an embodiment of the present invention.

FIG. 3 shows exemplary auto-contouring results, according to an embodiment of the present invention. 44 3D CT images from 11 patients are processed to evaluate the disclosed method and system, and each patient has at least 3 treatment images. Referring to FIG. 3, auto-segmentation results for 3 patients are shown from top to bottom (row A, B, and C correspond to patent A, B, and C, respectively). Each patient has three snapshots of its axial, sagittal and coronal planes (column 1, 2, and 3 correspond to the three snapshots, respectively). Auto-contouring results (in red) are compared with the experts' manual contours (in yellow). The average DICE achieves 0.93 for the prostate.

Figure 4:
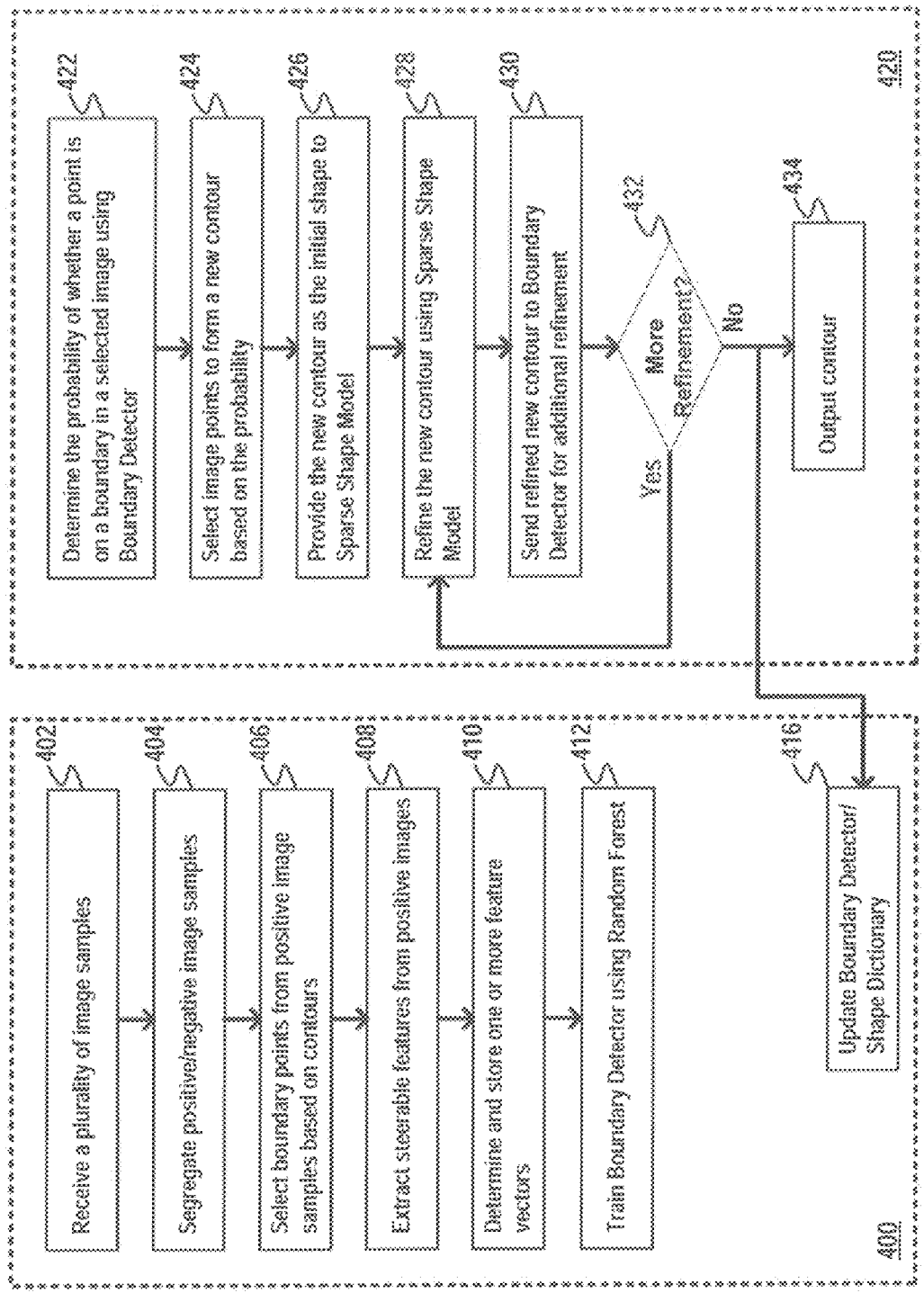
FIG. 4 is a flow chart of an exemplary method for performing auto-contouring, according to an embodiment of the present invention.

FIG. 4 is a flow chart of an exemplary method for performing auto-contouring, according to an embodiment of the present invention. In FIG. 4, a series of steps are shown to perform the disclosed method, some of which may be optional. FIG. 4 shows a training/updating subroutine 400 and a contouring subroutine 420. In some embodiments, training/updating subroutine 400 may be performed offline, for example, when the system is not receiving new images from CT scanner. In step 402, the system may receive a plurality of image samples. The image samples may include 3D CT images from the same patient or from different patients. In step 404, the image samples may then be segregated into positive and negative image samples based on, for example, manual contours provided by experts or auto contours generated by computer programs. Positive image samples may include image points that are on the contours, while negative image samples may include image points that are far away from the contours. In step 406, the system may select boundary points from positive image samples based on the contours provided by experts or computer programs. In step 408, the system may extract 3D steerable features from the selected boundary points in the positive image samples. 3D steerable features are known to be rotation-invariant. These features are extracted from a cube region around each sampled voxel. The orientation of the cube follows the normal direction of the sampled voxel. The features are extracted from each cube, and stored as a feature vector for each sampled voxel. In step 410, the system may determine one or more feature vectors based on the extracted steerable features and store the feature vectors. In step 412, the system may use random forest algorithm to train the boundary detector on the collected image samples.

Once the patient-specific boundary detector is generated, the patient-specific boundary detector may be used in the online subroutine 420, for example, when the system receives new images from CT scanner. When a new image is received, the process proceeds to step 422, in which the process includes searching along the normal direction of the new image, and using the patient-specific boundary detector to determine for each point whether it is on the boundary or not. For example, the system may determine the probability of whether a point is on the boundary in the image using the patient specific boundary detector. In step 424, the system may select image points to form a new contour based on the probability. For example, the system may select points with the highest probability to form a new boundary point. In another example, the system may select points with the probability higher than a predetermined threshold to form a new boundary point. In step 426, the system may provide the new contour, e.g., formed by the new boundary points selected in step 424, to the sparse shape dictionary 214 for refinement. For example, the new contour may be provided as the initial shape to the sparse shape model. In step 428, the system may refine the new contour using the sparse shape model. In some embodiments, the refinement is performed iteratively. In step 430, the refined new contour may be sent back to the patient-specific boundary detector for additional shape refinement. Then in step 432, the system determines whether additional iteration of refinement is need. If it is determined that additional refinement is needed, then the process proceeds back to step 428 and the contour will undergo a new round of refinement using the sparse shape model. If not, then the process proceeds to step 434 to output a final image including a final contour. The final image may be used to update patient specific boundary detector and/or the shape dictionary, as shown in step 416. The updating of the boundary detector is similar to training the initial boundary detector, except that the image samples now include the final image generated by subroutine 420. The updating of shape dictionary employs a subset of shapes using block-coordinate descent method, as previously disclosed.

Figure 5:
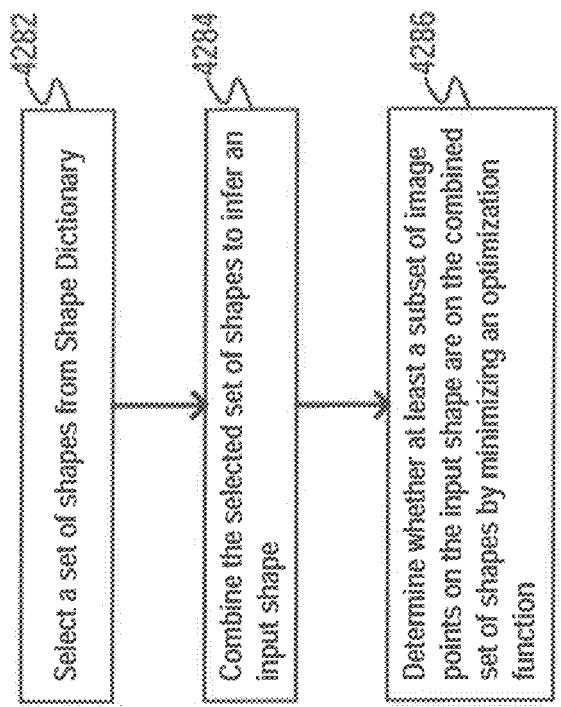
FIG. 5 is a flow chart of an exemplary method for performing contour refinement, according to an embodiment of the present invention.

FIG. 5 is a flow chart of an exemplary method for performing contour refinement, according to an embodiment of the present invention. In FIG. 5, step 428 of FIG. 4 is further divided into three substeps. In step 4282, the system may select a set of shapes (e.g., 3D shapes) from shape dictionary. In step 4284, the system may combine the selected set of shapes to approximate or infer an input shape, in this case the new contour provided in step 426 of FIG. 4. In step 4286, the system may determine whether at least a subset of image points on the input shape are on the combined set of shapes by minimizing an optimization function such as, for example, function (1). The combination of the shapes can then be sent back to boundary detector for additional refinement, as shown in step 430 of FIG. 4.

Figure 6:
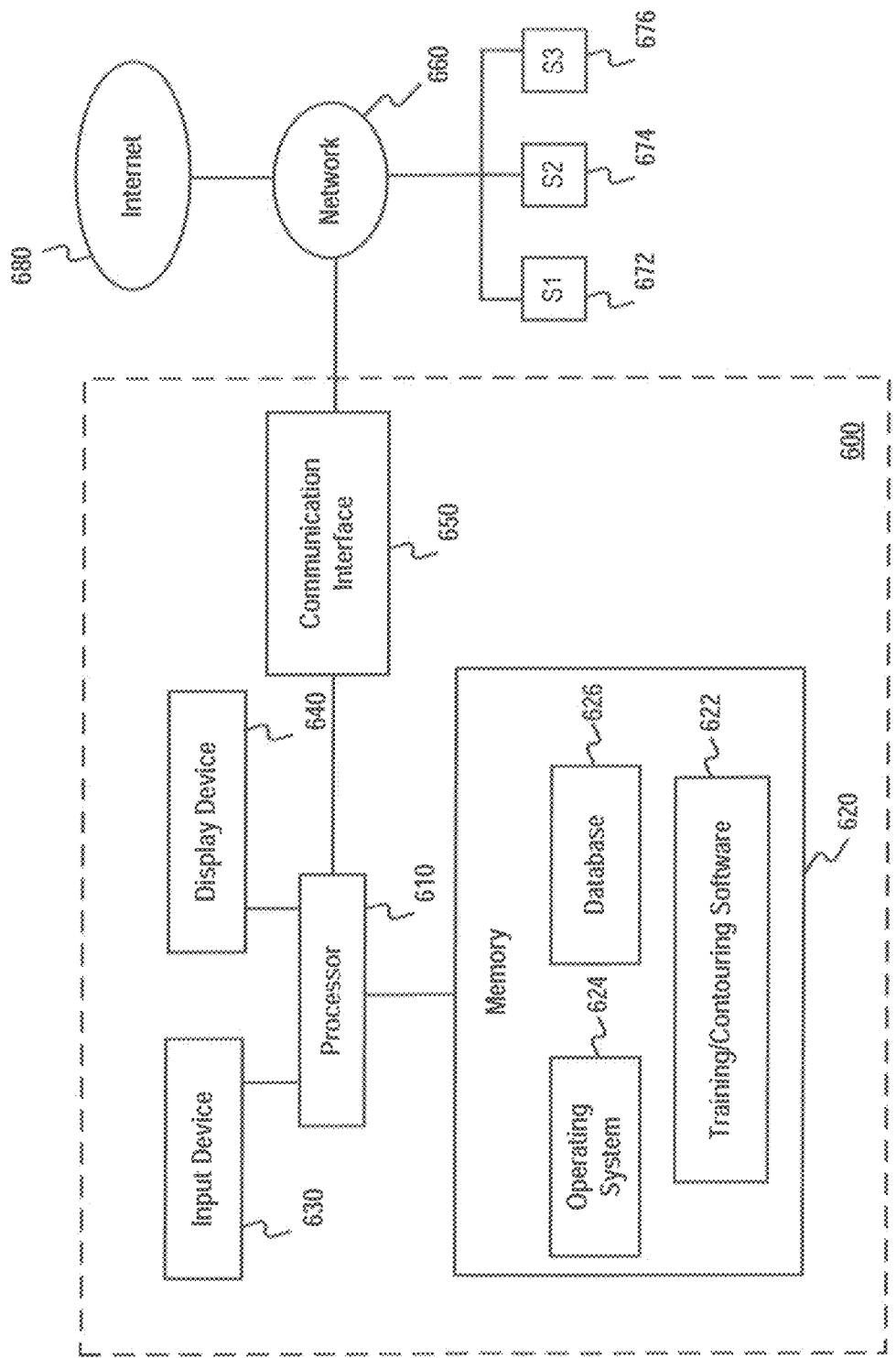
FIG. 6 is a schematic diagram of an exemplary auto-contouring system, according to an embodiment of the present invention.

FIG. 6 illustrates an exemplary system 600 for performing contour refinement. Consistent with some embodiments, system 600 may be a general purpose computer, or a computing device dedicated for auto-contouring. As shown in FIG. 6, system 600 may include a processor 610, a memory module 620, a user input device 630, a display device 640, and a communication interface 650. Processor 610 can be a central processing unit ("CPU") or a graphic processing unit ("GPU"). Depending on the type of hardware being used, processor 610 can include one or more printed circuit boards, and/or a microprocessor chip. Processor 610 can execute sequences of computer program instructions to perform various methods that will be explained in greater detail below.

Memory module 620 can include, among other things, a random access memory ("RAM") and a read-only memory ("ROM"). The computer program instructions can be accessed and read from the ROM, or any other suitable memory location, and loaded into the RAM for execution by processor 610. For example, memory module 620 may store one or more software applications. Software applications stored in memory module 620 may comprise operating system 624 for common computer systems as well as for software-controlled devices. Further, memory module may store an entire software application or only a part of a software application that is executable by processor 610.

In some embodiments, memory module 620 may store training and/or contouring software 622 that may be executed by processor 610. For example, training/contouring software 622 may be executed to train boundary detector 212, shape dictionary 214; perform auto-contouring in images 232-236, and/or perform updating to boundary detector 212, shape dictionary 214. It is also contemplated that training/contouring software 622 or portions of it may be stored on a removable computer readable medium, such as a hard drive, computer disk, CD-ROM, DVD±R, CD±RW or DVD±RW, HD or Blu-ray DVD, USB flash drive, SD card, memory stick, or any other suitable medium, and may run on any suitable component of system 600. For example, portions of training/contouring software 622 may reside on a removable computer readable medium and be read and acted upon by processor 610 using routines that have been copied to memory 620.

In some embodiments, memory module 620 may also store master data, user data, application data and/or program code. For example, memory module 620 may store a database 626 having therein various data used for performing training/updating/contouring.

In some embodiments, input device 630 and display device 640 may be coupled to processor 610 through appropriate interfacing circuitry. In some embodiments, input device 630 may be a hardware keyboard, a keypad, or a touch screen, through which a user may input information to system 600. Display device 640 may include one or more display screens that display the simulation interface, result, or any related information to the user.

Communication interface 650 may provide communication connections such that system 600 may exchange data with external devices. For example, system 600 may be connected to network 660. Network 660 may be a LAN or WAN that may include other systems S1 (672), S2 (674), and S3 (676). Systems S1, S2, and/or S3 may be identical to system 600, or may be different systems. In some embodiments, one or more of systems in network 660 may form a distributed computing/simulation environment that collaboratively performs training/updating/contouring task. In some embodiments, one or more systems S1, S2, and S3 may include a CT scanner that obtain CT images (e.g., image 232). In addition, network 660 may be connected to Internet 680 to communicate with servers or clients that reside remotely on the Internet.

In the foregoing descriptions, various aspects, steps, or components are grouped together in a single embodiment for purposes of illustrations. The disclosure is not to be interpreted as requiring all of the disclosed variations for the claimed subject matter. The following claims are incorporated into this Description of the Exemplary Embodiments, with each claim standing on its own as a separate embodiment of the invention.

Moreover, it will be apparent to those skilled in the an from consideration of the specification and practice of the present disclosure that various modifications and variations can be made to the disclosed systems and methods without departing from the scope of the disclosure, as claimed. Thus, it is intended that the specification and examples be considered as exemplary only, with a true scope of the present disclosure being indicated by the following claims and their equivalents.

What is claimed is:

1. A method, implemented by a processor, for performing auto-contouring in a medical image, the method comprising:
   receiving the medical image, wherein the medical image contains a region of interest and a plurality of voxels;
   identifying, by the processor, voxels of the medical image which are on a surface of the region of interest;
   selecting, by the processor, a first set of the identified voxels to form a first contour;
   refining the first contour, by the processor, based on a shape dictionary, to generate a second contour of the region of interest;
   updating a boundary detector based on a seconds set of the identified voxels, the second set being located along the second contour; and
   applying the updated boundary detector to auto-contour the region of interest in the medical image.

2. The method of claim 1, further including refining, by the processor, the second contour using the boundary detector.

3. The method of claim 1, wherein:
   identifying voxels of the medical image which are on the surface of the region of interest includes determining a probability of the voxels being on the surface of the region of interest; and
   selecting the first set of the identified voxels includes selecting voxels having probabilities higher than a predetermined threshold.

4. The method of claim 1, wherein refining, by the processor, the first contour based on the shape dictionary to generate the second contour includes:
   selecting a set of shapes from the shape dictionary;
   combining the selected set of shapes to approximate the first contour; and
   generating the second contour based on the combined set of shapes.

5. The method of claim 4, further including:
   determining whether at least a subset of voxels on the first contour are on the second contour by minimizing an optimization function.

6. The method of claim 1, wherein updating the boundary detector includes:
   comparing the medical image having the second contour with a collection of stored images containing the region of interest;
   selecting a subset of stored images with similar image structure to the medical image having the second contour; and
   updating the boundary detector based on the medical image having the second contour and the selected subset of stored images.

7. The method of claim 6, wherein updating the boundary detector includes:
   selecting voxels located on surfaces of the selected subset of stored images;
   extracting steerable features from the selected voxels located on sufaces of the selected subset of stored images;
   determining a feature vector based on the extracted steerable features; and
   updating the boundary detector based on the feature vector.

8. The method of claim 1, further including updating the shape dictionary based on the second contour, wherein updating the shape dictionary includes:
   selecting a subset of shapes from the medical image containing the second contour;
   obtaining a sparse coefficient for each shape in the subset; and
   updating the shape dictionary based on the obtained sparse coefficients.

9. The method of claim 1, wherein updating the boundary detector includes:
   (a) after updating the boundary detector based on the second contour, determining an updated first contour;
   (b) refining the updated first contour based on the shape dictionary to generate an updated second contour; and
   repeating steps (a) and (b) until a number of repetitions reaches a predetermined value.

10. The method of claim 1, wherein updating the boundary detector includes:
   (a) after updating the boundary detector based on the second contour, determining an updated first contour;
   (b) refining the updated first contour based on the shape dictionary to generate an updated second contour: and
   repeating steps (a) and (b) until a residual error reaches a predetermined minimum.

11. A system for performing auto-contouring in a medical image, comprising:
   a processor;
   a memory operatively coupled to the processor and storing instructions, that when executed by the processor, causes the processor to perform a method, the method comprising:
      receiving the medical image, wherein the medical image contains a region of interest and a plurality of voxels;
      identifying voxels. of the medical image which are on a surface of the region of interest;
      selecting a first set of the identified voxels to form first contour;
      refining the first contour based on a shape dictionary to generate a second contour of the region of interest;
      updating a boundary detector based on a second set of the identified voxels, the second set being located along the second contour; and
      applying the updated boundary detector to auto contour the region of interest in the medical image.

12. The system of claim 11, wherein identifying voxels of the medical image includes determining a probability of the voxels being on the surface; and selecting voxels having probabilities higher than a predetermined threshold.

13. The system of claim 11, wherein refining the first contour based on the shape dictionary to generate the second contour of the region of interest includes:
   selecting a set of shapes from the shape dictionary;
   combining the selected set of shapes to approximate the first contour; and
   generating the second contour based on the combined set of shapes.

14. The system of claim 13, wherein the method performed by the processor further includes:
   determining whether at least a subset of voxels on the first contour are on the second contour by minimizing an optimization function.

15. The system of claim 11, wherein the method performed by the processor further includes refining the second contour using the boundary detector.

16. The system of claim 11, wherein updating the boundary detector includes:
   (a) after updating the boundary detector based on the second contour, determining an updated first contour;
   (b) refining the updated first contour based on the shape dictionary to generate an updated second contour; and
   repeating steps (a) and (b) until a number of repetitions reaches a predetermined value.

17. The system of claim 11, wherein updating the boundary detector includes:
   (a) after updating the boundary detector based on the second contour, determining an updated first contour:
   (b) refining the updated first contour based on the shape dictionary to generate an updated second contour; and
   repeating steps (a) and (b) until a residual error reaches a predetermined minimum.

18. A computer-implemented method for training a boundary detector based on a plurality of medical images containing a region of interest, the method comprising:
   selecting, by a processor from the plurality of medical images, voxels located on a contour surface of the region of interest
   extracting, by the processor, steerable features from the selected voxels;
   determining, by the processor, a feature vector based on the extracted steerable features; and
   generating, by the processor, the boundary detector based on the feature vector.

19. The computer-implemented method of claim 18, comprising:
   comparing a new image having a new contour surface with the plurality of medical images;
   selecting a subset of medical images from the plurality of medical images based on image structure of the new image; and
   updating the boundary detector based on the new image and the selected subset of medical images.

20. The computer-implemented method of claim 19, further including:
   selecting a subset of shapes from the new image;
   obtaining sparse coefficients for shapes in the subset; and
   updating a shape dictionary based on the obtained sparse coefficients.

* * * * *

UNITED STATES PATENT AND TRADEMARK OFFICE
CERTIFICATE OF CORRECTION

| | |
|---|---|
| PATENT NO. | : 9,629,598 B2 |
| APPLICATION NO. | : 14/192778 |
| DATED | : April 25, 2017 |
| INVENTOR(S) | : Yan Zhou et al. |

It is certified that error appears in the above-identified patent and that said Letters Patent is hereby corrected as shown below:

In the Claims

Claim 11, Column 11, Lines 13-14, "voxels to form first contour" should read --voxels to form a first contour--.

Claim 18, Column 12, Line 21, "region of interest" should read --region of interest;--.

Signed and Sealed this
Fifth Day of September, 2017

Joseph Matal
*Performing the Functions and Duties of the*
*Under Secretary of Commerce for Intellectual Property and*
*Director of the United States Patent and Trademark Office*